United States Patent [19]
Borodulin et al.

[11] Patent Number: 5,806,527
[45] Date of Patent: Sep. 15, 1998

[54] URETHRAL PLUG WITH MEANS FOR PROTECTION AGAINST INFECTION

[76] Inventors: German Borodulin, 583-46th Ave., San Francisco, Calif. 94121; Alexander Shkolnik, 485 Dartmouth Ave., San Carlos, Calif. 94070

[21] Appl. No.: 869,290

[22] Filed: Jun. 4, 1997

[51] Int. Cl.[6] .................................................. A61F 5/48
[52] U.S. Cl. ........................ 128/885; 128/DIG. 25; 600/29
[58] Field of Search ............................ 128/885, 886, 128/DIG. 25; 600/29–31

[56] References Cited

U.S. PATENT DOCUMENTS

| | | | |
|---|---|---|---|
| 3,347,234 | 10/1967 | Voss | 604/18 |
| 3,699,962 | 10/1972 | Hanke | 604/18 |
| 4,969,474 | 11/1990 | Schwarz | 128/885 |
| 5,671,755 | 9/1997 | Simon | 128/885 |

Primary Examiner—Michael A. Brown

[57] ABSTRACT

The female urinary plug (10) of the invention includes a catheter (10) with an infection-protective cap (12) fitted on the distal end (D) of the catheter insertable into the urinary bladder through the urethra (U). The catheter (10) has a soft inflatable balloon (14) on its distal end (D) and a preinflated hard balloon (18) on its proximal end (P). Prior to insertion, the inflation of the soft balloon is prevented by the inner walls of the infection-protective cap (12). The distal end of the cap (12) has a collet-like shape and is provided with expandable petal-like tongues (36a, 36b, and 36c). Normally these resilient tongues are in a closed state. When the plug is inserted into the urethra and further movement of the cap (12) is prevented due to its contact with the patient's body in the area of the orificium of the urethra, the continuing movement of the catheter (10) releases the soft inflatable balloon (14) from the cap, whereby after penetration into the urinary bladder it is inflated by compressed air contained in the preinflated hard balloon (18) and the catheter (10). In the urinary bladder, soft inflated balloon 14 rests on the walls of the urinary bladder and holds the plug in place, until the patient deflates this balloon by opening a check valve (20) on the external part of the plug.

12 Claims, 2 Drawing Sheets

URETHRAL PLUG WITH MEANS FOR PROTECTION AGAINST INFECTION

FIELD OF THE INVENTION

The present invention relates to the field of urology, in particular to means for preventing involuntary loss of urine from the urinary bladder of female patients suffering from urinary incontinence. More specifically, the invention relates to a urethral a with a balloon and to a method for protection against infection during the use of this plug.

DESCRIPTION OF THE PRIOR ART

According to the latest statistical data, between 10 and 20 million people suffer in United States alone from various types of voiding dysfunctions. Among them about 75% are females.

At the present time, many different types of treatment are used for treating urinary incontinence. In general all these methods of treatment can be roughly divided into two groups: conservative and surgical. Examples of conservative methods are drug therapy, biofeed-back therapy, exercise therapy, electrical stimulation, vibratory stimulation, use of protective pads, etc. Surgical methods include more than 50 different modalities. Nevertheless, conservative treatment is preferable as a first-choice therapy because of a high rate of complications after the surgery.

Both these methods, however, are still not satisfactory in many cases, and complications are not unusual. In view of the above, there is always a need in new progressive conservative methods of treatment of urinary incontinence.

One of the last developments in this field is the use of a urethral plug for prevention of involuntary loss of urine. Such plugs are produced, e.g., by UroMed Corporation, Needham, Mass. under the trademark Reliance®. The UroMed plug consists of a catheter with a balloon at the distal end, which is inflatable with the use of a syringe. The patient inserts the catheter through the urethra so that its distal end penetrates the urinary bladder. The inflated balloon rests on the bladder neck and is designed to block the flow of urine. Then the balloon is inflated by means of a syringe via an external proximal end of the plug. The use of a syringe is extremely inconvenient. In addition, the patient needs that the syringe be always available. To remove the plug, it is necessary to pool the attached string to deflate the balloon. This is also inconvenient.

A female urethra is approximately 4 cm long. It is known that the meatus and the first third portion of the female's urethra is a harbor for different bacteria. Therefore, during catheterization the urethral flora is pushed into the bladder, and this can initiate a urinary infection. For the above reason, the urethral catheter is the cause of hundreds of thousands of urinary-tract infections each year in this country alone. In healthy subjects, even after single catheterization, the rate of infection is 1 to 2%, but this rises to 15% in elderly bedridden females and as high as 40% in females with urinary obstruction during labor. The problem is aggravated if the catheter is maintained in the urethra for a long period of time. Therefore the use of the aforementioned urethral plug does not exclude the occurrence of the infections in the rates described above.

Experience shows that sterilization of the urethra by instillation of antibiotics into the urethra before catheterization does not satisfactorily solve the above problems and the benefits of such sterilization are questionable.

OBJECTS OF THE INVENTION

It is an object of the invention to provide a urethral plug for management of urinary incontinence which prevents the transfer of the urethral flora into the urinary bladder, excludes the use of a syringe for inflation of the balloon, simplifies the deflation of the balloon, and reduces the risk of complications cause by the infection in the urinary system. Another object is to provide a method or protection against infection in conjunction with the use of urinary catheter. Still another object is to provide an improve method for preventing involuntary loss of urine in female patients suffering from urinary. An additional object is to provide an infection-protective cap insertable into a female urethra for protecting the urethra and urinary bladder against transfer of infection bacteria.

These and other objects and advantages of the present invention will become apparent after the consideration of the following description with reference to the accompanying drawings.

SUMMARY OF THE INVENTION

The female urinary plug of the invention comprises a catheter with an infection-protective cap fitted on the distal end of the catheter insertable into the urinary bladder through the urethra. The catheter has a soft inflatable balloon on its distal end and a preinflated hard balloon on its proximal end. Prior to insertion, the inflation of the soft balloon is prevented by the inner walls of the infection-protective cap. The distal end of the cap has a collet-like shape and is provided with expandable petal-like tongues. Normally these resilient tongues are in a closed state. When the plug is inserted and further movement of the cap is prevented due to its contact with the patient's body in the area of the oricium of the urethra, the continuing movement of the catheter releases the soft inflatable balloon from the cap, whereby the latter is inflated by compressed air in the preinflated hard balloon and the catheter. When the inflated balloon penetrates the urinary bladder, it rests on the walls of the urinary bladder and holds the plug in place, until the patient deflates this balloon by opening a check valve on the external part of the plug.

DETAILED DESCRIPTION OF THE INVENTION

Figure 1:
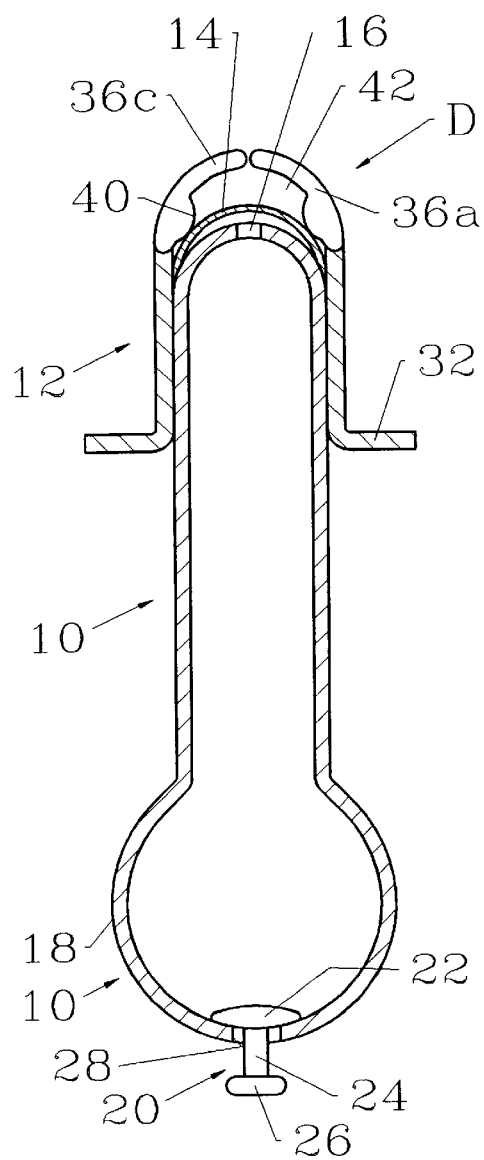
FIG. 1 is a longitudinal sectional view of the urinary plug of the invention.
Figure 2:
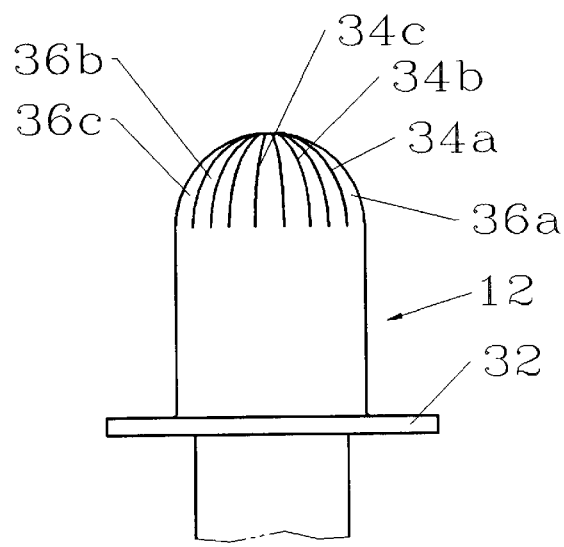
FIG. 2 is a fragmental view of the plug of FIG. 1 illustrating the collet-like distal end of the infection-protective cap with petals in a closed state.
Figure 4:
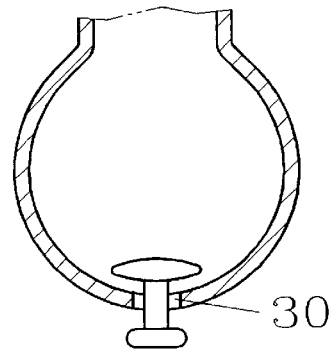
FIG. 4 is a partial view of the proximal end of the plug with the valve open for deflating the soft inflatable balloon.

As shown in FIG. 1, the urethral plug of the invention consists essentially of two main parts, i.e., of a catheter portion 10 and an infection protective cap 12 which is telescopically fitted onto the distal end of catheter portion 10.

Catheter portion 10 has on its distal end D an inner soft inflatable balloon 14 with thin resilient walls. The interior of inner soft balloon 14 and the interior of catheter portion 10 are connected via an opening 16 in the front end of catheter portion 10. On its proximal end P, catheter portion 10 has an outer hard inflatable balloon 18 with the walls thicker and more rigid than the walls of inner soft balloon 14.

A check valve 20 is installed in the rear wall of outer hard balloon 18. Check valve 20 has a very simple construction. It consists of a plate valve element 22 which is pressed to the inner wall of outer hard balloon 18 by compressed air which fills balloon 18, catheter portion 10, and inner soft balloon 14. Plate valve element 22 has a stem portion 24 and a push button 26 which projects to the outside from outer hard balloon 18. The diameter of an opening 28 through which stem portion 24 passes to the outside of the outer hard balloon is larger than the diameter of stem portion 24. When the interior of catheter portion 10, and of both balloons 14 and 18 is filled with air under pressure, the passage 30 formed between stem portion 24 and the inner walls of opening 28 is closed by plate valve element 22 under pressure of air.

Catheter portion 10 is made of a soft medically-acceptable thermoplastic elastomer. The balloons are made of rubber and are sealingly connected to external walls of catheter portion.

Infection protective cap 12 is also made of the same material as the catheter portion. It has a flanged rear portion 32 which is used as a stopper for further movement of protective cap 12 against the surface of the patient's body around the orificium of the urethra (not shown). On its front or distal end, infection protective cap 12 has a collet-like structure formed by longitudinal cuts 34a, 34b, 34c, . . . which form petals 36a, 36b, 36c, . . . These petals are resilient and in a normal state tend to approach each other so as to close an opening 38 at the apex of infection protective cap.

On its inner wall near the distal end, infection protective cap 12 has a shoulder 40 which defines a small space 42 between the inner walls of petals 36a, 36b, 26c . . . and the front end of inner soft balloon 14, but which does not prevent further movement of catheter portion 10 with inner soft balloon 14 forward into the urethra and urinary bladder through the front portion of infection protective cap 12 when a pushing force is applied to the catheter portion with the protective cap stopped.

Infection protective cap 12 may have a lengths of one to two-thirds of the initial part of a female urethra, i.e., the most infectious portion of the urethra.

The entire plug is contained in a sealed package (not shown) and is sterile and disposable.

Prior to use, the sterile and disposable urethral plug of the invention is removed from a sealed plastic package (not shown). The plug has a preinflated outer hard balloon 18 and infection protective cap 12 fitted onto distal end D of catheter portion 10. In this state, the front end of inner soft balloon 14 is in contact with shoulder 40. Inner soft balloon 14 cannot be inflated under the effect of pressure of air inside inflated outer hard balloon 18 because its expansion is restricted by hard petals 36a, 36b, 36c of a collet-like front end of infection protective cap 12. The outer surface of plug 12 is prelubricated prior to packaging.

The urethral plug of the invention is then inserted into the urethra of a patient suffering from urinary incontinence. In the course of insertion, flange 32 stops against the patient's body around the orificium of the urethra U (FIG. 3) whereby further movement of protective cap 12 is impossible. In this position the cap covers the walls of the most infectious portion of the urethra U.

Now, for further movement of catheter portion 10 into the urethra, the user pushes catheter portion 10 forward in the same direction by holding the outer inflated portion 18 as a handle. In this case, the forward or distal end of catheter portion 10 moves petals 36a, 36b, 36c apart, thus enlarging opening 42 and allowing inner soft balloon 14 to inflate under the effect of pressure of air inside outer balloon 18 and catheter portion 10. In the course of passage through the distal expandable portion of infection-protective cap 12, the sterile tip of main catheter portion 10 does not have physical contact with inner surfaces of petals 36a, 36b, 36c . . . since they are moved apart to a sufficient distance. This is achieved due to a provision of shoulder 40. Space 42 also prevents contact of the infected portion of the cap with the tip of the main catheter portion.

Figure 3:
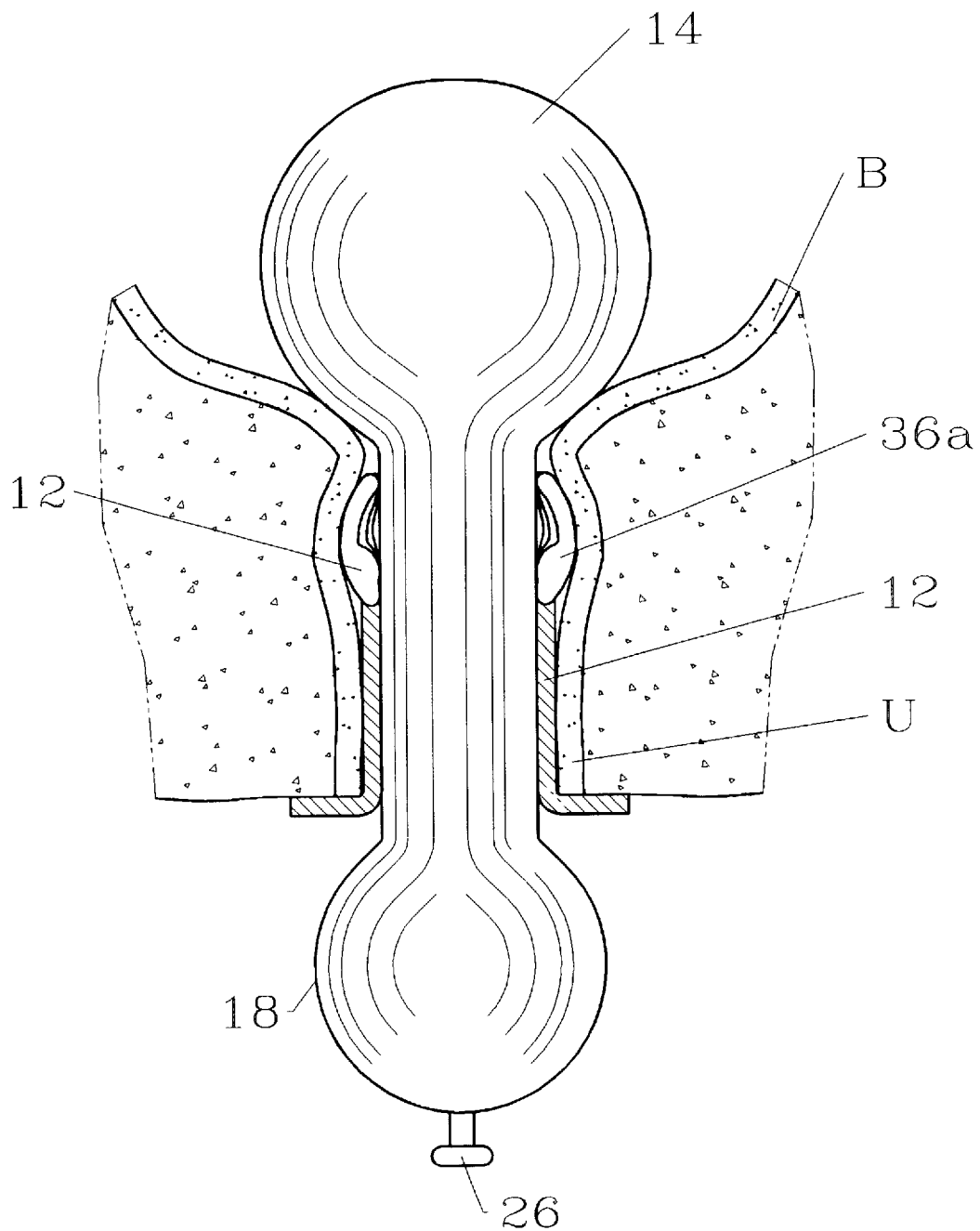
FIG. 3 is a side view of the plug of FIG. 1 in dwelling position with a soft balloon inflated and resting on the walls of the urinary bladder.

As a result, inner soft balloon 14 inflates and assumes a position shown in FIG. 3 in the urinary bladder B. In the dwelling state, the plug is kept inside the urinary bladder B by soft inner balloon 14, whereas its further penetration into the bladder is prevented by outer hard balloon 18.

Thus it has been shown that the invention provides a urethral plug for management of urinary incontinence which prevents the transfer of the urethral flora into the urinary bladder, excludes the use of a syringe for inflation of the balloon, simplifies the deflation of the balloon, and reduces the risk of complications cause by the infection in the urinary system.

Although the invention has been shown and described with reference to specific examples, it is understood that these examples should not be construed as limiting the scope of the invention, and many other modifications are possible. For example, check valve 20 may have a different construction. The distal end of protective cap 12 may have only one slit instead of plurality of petals. Infection-protective cap 12 may be used not necessarily in conjunction with the catheter-type incontinence-preventive plug shown and described in the present patent application, but also for guiding through and for introduction into a female urethra of any urological instruments or catheters, such as instruments and catheters for transurethral procedures and operations. In other words, the protective cap of the plug of the invention prevents physical contact of such instruments and catheters with the most infectious portion of the female urethra. Therefore the scope of the invention is defined not by the examples given but by the patent claims and their legal equivalents.

We claim:

1. A urethral plug for preventing involuntary loss of urine from the urinary bladder of a female patient, comprising:

a main catheter portion having a distal end which is to be inserted into a female urethra and a proximal end which remains outside of the urethra when the plug is in an inserted position; and an infection-protective cap which is insertable into said urethra and which is fitted onto said distal end of said main catheter portion, said infection-protective cap having a distal end and a proximal end;

said main catheter portion having a soft inflatable balloon on said distal end of said main catheter portion and a hard preinflated balloon on said proximal end of said main catheter portion, said soft inflatable balloon being normally located inside said infection-protective cap which prevents its inflation;

said hard preinflated balloon having a check valve which is normally closed but can release air from the interior of said soft inflatable balloon, said main catheter portion, and said hard preinflated balloon when said check valve is activated;

said infection-protective cap having a flange on its proximal end for stopping said infection-protective cap against the body of said patient when further movement of said infection-protective cap becomes impossible; and at least one slit on said distal end of said infection-protective cap for passing said distal end of said main catheter body with said soft inflatable balloon through said slit when said infection-protective cap is stopped.

2. The urethral plug of claim 1, wherein said soft inflatable balloon is sealingly attached to said distal end of said main cathet portion and communicates therewith through an opening at said distal end of said main catheter portion.

3. The urethral plug of claim 1, wherein said distal end of said infection-protective plug has slits that form petals which normally are closed toward each other and define a space which prevents physical contact of said distal end of said main catheter portion with the inner surfaces of said petals.

4. The urethral plug of claim 3, wherein said petals have shoulders on their inner surfaces for moving said petals further apart from contact with said distal end of said main catheter portion when said main catheter portion is pushed through said distal end of said infection-protective cap.

5. The urethral plug of claim 4, wherein said infection-protective cap has a length from one third to two thirds of the length of a female urethra.

6. The urethral plug of claim 5, wherein said main catheter portion and said infection-protective cap are sterile and disposable.

7. The urethral plug of claim 1, wherein said main catheter portion and said infection-protective cap are sterile and disposable.

8. The urethral plug of claim 7, wherein said infection-protective cap has a length from one third to two thirds of the length of a female urethra.

9. A method for protection against introduction of infection bacteria into the urethra of a female patient in conjunction with the use of urological instruments and catheters insertable into and through said urethra, comprising the steps of:

providing an infection-protective cap insertable into said urethra, said cap having a distal end and a proximal end with a flange, said distal end having at least one slit for passing said urological instruments and catheters into and through said urethra, said infection-protective cap being sterile and disposable, said slit having mating sides;

inserting said infection-protective cap into the infectious portion of said urethra until said flange is stopped against the body of said patient around orificium of said urethra;

guiding said urological instruments and catheters through said slit into and through said urethra when said infection-protective cap is stopped, thus spreading said mating sides of said slit apart and preventing physical contact of said urological instruments and catheters with said infectious portion of said urethra.

10. The method of claim 9, further including the steps of:

providing said distal end of said infection-protective cap with inner shoulders;

bringing said urological instruments and catheters in contact with said shoulders when said urological instruments and catheters are inserted into said urethra through said at least one slit; and spreading said mating parts of said slit further apart by acting on said shoulders with said urological instruments and catheters thus preventing physical contact of said urological instruments and catheters with said distal end of said infection-preventive cap.

11. A method for preventing an involuntary loss of urine in female patients suffering from urinary incontinence, comprising:

providing a urethral plug comprising a main catheter portion which has a distal end and a proximal end and an infection-protective cap fitted onto said distal end of said main catheter portion, said infection-protective cap having a distal end and a proximal end with a flange, said distal end of said infection-protective cap having at least one slit sufficient to pass said main catheter portion, said main catheter portion having a soft inflatable balloon on said distal end of said main catheter portion and a hard preinflated balloon on said proximal end of said main catheter portion, said soft inflatable balloon being normally located inside said infection-protective cap which prevents its inflation, said hard preinflated balloon having a check valve which is normally closed, said infection-protective cap having a flange on its proximal end;

inserting said urinary plug into said urethra until said flange is stopped against the body of said patient;

pushing said main catheter body with said soft inflatable balloon through said slit into said urethra and further into the urinary bladder when said infection-protective cap is stopped;

allowing said soft inflatable balloon to inflate when it is released from said infection-protective cap, thus closing the opening of said urinary bladder due to contact of said soft inflatable balloon with the neck of said urinary bladder, and closing the orificium of said urethra due to contact of said hard preinflated balloon with the body of said patient around the orificium of said urethra.

12. The method of claim 11, further including the steps of:

opening said check valve;

deflating said soft inflatable balloon; and removing said urinary plug from said urinary bladder and said urethra.

* * * * *